United States Patent [19]

Daniels et al.

[11] Patent Number: 5,725,863
[45] Date of Patent: Mar. 10, 1998

[54] POLYPEPTIDES USEFUL IN PREVENTION OF CHLAMYDIA INFECTION

[75] Inventors: Eddie K. Daniels, Hastings; Neal E. Woollen, Harvard, both of Nebr.

[73] Assignee: The United States of America as represented by the Secretary of Agriculture, Washington, D.C.

[21] Appl. No.: 756,346

[22] Filed: Sep. 6, 1991

[51] Int. Cl.$^6$ .................. A61K 39/118; C07K 14/295
[52] U.S. Cl. .................. 424/263.1; 424/185.1; 530/350; 530/389.5; 530/412; 530/825
[58] Field of Search .................. 424/88, 92, 185.1, 424/263.1; 514/2; 530/350, 389.5, 412, 825

[56] References Cited

U.S. PATENT DOCUMENTS

| | | | |
|---|---|---|---|
| 4,118,469 | 10/1978 | Caldwell et al. | 424/1 |
| 4,267,170 | 5/1981 | Seawell | 424/88 |
| 4,271,146 | 6/1981 | Seawell | 424/89 |
| 4,386,065 | 5/1983 | Waldhalm | 424/89 |
| 4,427,782 | 1/1984 | Caldwell et al. | 436/542 |
| 4,497,899 | 2/1985 | Armstrong et al. | 436/510 |
| 4,663,291 | 5/1987 | Rose | 435/259 |
| 4,766,065 | 8/1988 | Mosier et al. | 435/7 |
| 4,916,057 | 4/1990 | Thompson et al. | 435/7 |

FOREIGN PATENT DOCUMENTS

| | | |
|---|---|---|
| 0017460 | 3/1980 | European Pat. Off. . |
| 0293079 | 4/1988 | European Pat. Off. . |
| 0348725 | 6/1989 | European Pat. Off. . |
| 0363106 | 9/1989 | European Pat. Off. . |
| 8800977 | 2/1988 | WIPO . |

OTHER PUBLICATIONS

Anderson et al., Efficacy Against Ovine Enzootic Abortin of an Experimental Vaccine Containing Purified Elementary Bodies of *Chlamydia psittaci*, Veterinary Microbiology 24:21–27 (1990).

Baehr et al, Mapping Antigenic Domains Expressed by *Chlamydia trachomatis* Major Outer Membrane Protein Genes, Proc. Natl. Acad. Sci U.S.A. 85:4000–4004 (1988).

Baghian et al, Antibody Response to Epitopes of Chlamydial Major Outer Membrane Proteins on Infectious Elementary Bodies and of the Reduced Polyacrylamide Gel Electrophoresis–Separated Form, Infection and Immunity 58:1379–1383 (1990).

U.S. application No. 07/324,664, Caldwell et al., filed Mar. 17, 1989.

Barron, Microbiology of Chlamydia.

Batteiger et al., Antigenic Analysis of the Major Outer Membrane Protein of *Chlamydia trachomatis* with Murine Monoclonal Antibodies, Infectino and Immunity 53:530–533 (1986).

Bavoil et al., Role of Disulfide Bonding in Outer Membrane Structure and Permeability in *Chlamydia trachomatis*, Infection and Immunity 44:479–485 (1984).

Blobel et al., Chlamydia, Handbuch der Bakteriellen Infektionen bei Tieren, Band V. 447–531 (1985).

Brade et al., Chemical, Biological, and Innunochemical Properties of the *Chlamydia psittaci* Lipoplysaccharide. Infection and Immunity 54:568–574 (1986).

Caldwell et al., Antigen Analysis of the Major Outer Membrane Protein of Chlamydia spp., Infection and Immunity 35:1024–1031 (1982).

Caldwell et al., Structural Analysis of Chlamydial Major Outer Membrane Proteins, Infection and Immunity 38:960–968 (1982).

Carlson et al., Cloning and Characterization of a *Chlamydia trachomatis* L3 DNA Fragment That Codes for an Antigenic Region of the Major Outer Membrane Protein and Specifically Hybridizes to the C–and C–Related–Complex Serovars, Infection and Immunity 57:487–494 (1989).

Chandler et al. I, A New Enzyme Immunoassay System Suitable for Field Use and Its Application in a Snake Venom Detection Kit, Clinica Chimica Acta 121:225–230 (1982).

Chandler et al. II, An Investigation of the Use of Urease–Antibody Conjugates in Enzyme Immunoassays, J. of Immunological Methods 53:187–194 (1982).

Conlan et al. I, Epitope Mapping with Solid–Phase Peptides: Identification of Type–, Subspecies–, Species–and Genus–Reactive Antibody Binding Domains on the Major Outer Membrane Protein of *Chlamydia trachomatis*, Molecular Microbiology 2(5):673–679 (1988).

Conlan et al. II, The major outer membrane protein of *Chlamydia trachomatis*: critical binding site and conformation determine the specificity of antibody binding to viable chlamydiae, Molecular Microbiology 3(3):311–318 (1989).

Dopfer et al., Vertraglichkeits–und immunisierungsversuche mit einer kommerziellen Vakzine gegen *Chlamydia psittaci* und *Coxiella burnetii*, Dtsch. tierarztl. Wschr. 93:267–269 (1986).

Favero, Biological Hazards in the Laboratory, Laboratory Medicine 18:665–670 (1987).

Filstein et al., Epidemic of Psittacosis in a College of Veterinary Medicine, JAVMA 179:569–572 (1981).

Fraiz et al., Chlamydial Infectios, Am. Rev. Med. 39:357–370 (1988).

Fudge, Update on Chlamydiosis, Veterinary Clinics of North America: Small Animal Practice 14:201–221 (1984).

Johnson et al. I, Abortion due to infection with *Chlamydia psittaci* in a sheep farmer's wife, British Medical Journal 290:592–595 (1985).

(List continued on next page.)

*Primary Examiner*—Thomas M. Cunningham
*Attorney, Agent, or Firm*—M. Howard Silverstein; Curtis P. Ribando; John D. Fado

[57] ABSTRACT

The present invention relates to a polypeptide vaccine and method to immunize subjects against Chlamydia. In particular, this invention relates to essentially pure polypeptides of *Chlamydia psittaci* strain DD-34 ranging from about 40 to 140 kilodaltons in a pharmaceutically acceptable carrier. These compositions are used to immunize several species of animals against Chlamydia. More specifically, this invention relates to the discovery of a highly immunogenic essentially pure polypeptide of *Chlamydia psittaci* strain DD-34 having a molecular weight of about 96 kilodaltons.

10 Claims, No Drawings

OTHER PUBLICATIONS

Johnson et al. II. Intracerebral Infection of Mice with Ovine Strains of *Chlamydia psittaci*: an Animal Screening Test for the Assay of Vaccines. J. Comp. Path. 96:497–505 (1986).

Kuo et al., Ultrascrutural Study of *Chlamydia trachomatis* Surface Antigens by Immunogold Staining with Monoclonal Antibodies. Infection and Immunity 55: 1324–1328 (1987).

Lagrange et al., Vaccines against Mycobacteria and Other Intracellular Multiplying Bacteria. Ann. Inst. Pasteur/Immunol. 136:151–162 (1985).

Larghi et al. I. Ethylenimine–Inactivated Rabies Vaccine of Tissue Culture Origin. J. Clin. Microbiology 3:26–33 (1967).

Larghi et al. II. Rabies Virus Inactivation by Binary Ethylenimine: New Method for Inactivated Vaccine Production. J. Clin. Microbiology 11:120–122 (1980).

Ma et al., Identification of conserved regions for species and subspecies specific epitopes on the major outer membrane protein of *Chlamydia trachomatis*. Microbial Pathogenesis 3:299–307 (1987).

MacDonald, Antigens of *Chlamydia trachomatis*, Reviews of Infectious Diseases 7:731–736 (1985).

Mahajan et al., Development of a Macromolecular Vaccine against Experimental Chlamydiosis and Berberine—a new anti–trachoma agent., 103–109 (1985).

Mohan. Epidemiologic and laboratory observations of *Chlamydia psittaci* infection in pet birds. JAVMA 184:1372–1374 (1984).

Moulder, The relation of the Psittacosis Group (Chlamydiae) to Bacteria and Viruses. Annual Review of Microbiology 20:107–130 (1966).

Nagington. Psittacosis/ornithosis in Cambridgeshire 1975–1983. J. Hyg., Camb. 92:9–19 (1984).

Nano et al., Partial Amino Acid Sequence and Molecular Cloning of the Encoding Gene for the Major Outer Membrane Protein of *Chlamydia trachomatis*, Infjection and Immunity 48:372–377 (1985).

Puy et al., Immunological specificity of monoclonal antibodies to *Chlamydia psittaci* ovine abortion strain. Immunology Letters 23:217–222 (1989/1990).

Rank et al., Protective Role of Serum Antibody in Immunity to Chlamydial Genital Infection. Infection Immunity 57:299–301 (1989).

Schachter. Overview of *Chlamydia trachomatis* Infection and the Requirements for a Vaccine. Reviews of Infectious Diseases 7:713–716 (1985).

Seki et al., Monoclonal Antibodies to *Chlamydia psittaci*: Characteristics and Antigenic Analysis. Jpn. J. Vet Sci. 50:383–393 (1988).

Smith et al., A modified ELISA that selectively detects monoclonal antibodies recognizing native antigen. J. of Immunological Methods 94:31–35 (1986).

Stephens et al. I. A species–specific major outer membrane protein domain. 110–113.

Stephens et al. II. High–Resolution Mapping of Serovar–Specific and Common Antigenic Determinants of the Major Outer Membrane Protein of *Chlamydia trachomatis*. J. Exp. Med. 167:817–831 (1988).

Storz. Chlamydia and Chlamydia–Induced Diseases (Charles C. Thomas Publishers 1971).

Su et al., Differential Effect of Trypsin on Infectivity of *Chlamydia trachomatis*: Loss of Infectivity Requires Cleavage of Major Outer Membrane Protein Variable Domains II and IV. Infection and Immunity 56:2094–2100 (1988).

Tan et al., Protection of Sheep against *Chlamydia psittaci* Infection with a Subcellular Vaccine Containing the Major Outer Membrane Protein. Infection and Immunity 58:3101–3108 (1990).

Taylor et al. I. Attempted Oral Immunization with Chlamydial Lipopolysaccharide Subunit Vaccine. Investigative Ophthalmology & Visual Science 28:1722–1726 (1987).

Taylor et al. II. Oral Immunization with Chlamydial Major Outer Membrane Protein (MOMP). Investigative Ophthalmology & Visual Science 29:1847–1853 (1988).

Toyofuku et al., Monoclonal Antibodies against *Chlamydia psittaci*. Microbiol. Immunol. 30:945–955 (1986).

Wenman et al., *Chlamydia trachomatis* Elementary Bodies Possess Proteins which Bind to Eucaryotic Cell Membranes. J. Bacteriology 165:602–607 (1986).

Yung et al., Psittacosis—a review of 135 cases. The Medical Journal of Australia 148:228–233 (1988).

Zhang et al. I. Protective Monoclonal Antibodies Recognize Epitopes Located on the Major Outer Membrane Protein of *Chlamydia trachomatis*. J. Immunology 138:575–581 (1987).

Zhang et al: II. The Low–Molecular–Mass, Cysteine–Rich Outer Membrane Protein of *Chlamydia trachomatis* Possesses Both Biovar–and Species–Specific Epitopes. Infection and Immunity 55:2570–2573 (1987).

Zhong et al. I. Immunaccessible Peptide Sequences of the Major Outer Membrane Protein from *Chlamydia trachomatis* Serovar C. Infection and Immunity 58:3438–3441 (1990).

Zhong et al. II. Mapping Antigenic Sites on the Outer Membrane Protein of *Chlamydia trachomatis* with Synthetic Peptides. Infection and Immunity 58:1450–1455 (1990).

POLYPEPTIDES USEFUL IN PREVENTION OF CHLAMYDIA INFECTION

BACKGROUND OF THE INVENTION

1. Field of the Invention

This invention relates generally to vaccines for veterinary use. In particular, it relates to Chlamydia vaccines useful for prevention and treatment of disease processes created or induced by Chlamydia organisms. In particular, this invention relates to essentially pure polypeptides of *Chlamydia psittaci* strain DD-34 in a pharmaceutically acceptable carrier and the use of this composition as a vaccine for a number of Chlamydia strains.

2. Description of the Prior Art

Chlamydia are unique organisms that infect a susceptible host by an infectious particle called an elementary body. An elementary body is small, approximately (200–300 nm) and is resistant to environmental factors. The organism attaches itself to the host cell and is ingested by a phagocytic process. Schachter, J., Overview of *Chlamydia trachomatis* Infection and Requirements for a Vaccine. Rev. Inf. Dis. 7:713 (1985).

Chlamydia are of medical and biological interest because of their unique interaction with eukaryotic host cells, and the diverse diseases they cause in man and animals. Blobel, H., T. Schlieber, Handbuch der bacteriellen Infection bei Tieren. Gustav Fisher Verlag Stuttgart, p. 447 (1985). Animals susceptible to *Chlamydia psittaci* infections are widely distributed in the animal kingdom, ranging from wild and domesticated birds and mammals to man. These infections have been identified as a cause of pneumonia, enteritis, encephalitis, conjunctivitis, and polyarthritis; abortions and genital disorders; and clinically unapparent infections. Blobel, H., T. Schlieber, Handbuch der bacteriellen Infection bei Tieren. Gustav Fisher Verlag Stuttgart, p. 447 (1985). Although *Chlamydia psittaci* is considered to be primarily a pathogen of animals other than man several strains have shown varying degrees of zoonotic potential. Filstein, M. R., Ley, A. B., Vernon, M. S., Goffney, A., Glickmen, L. T. Epidemic of Psittacosis in a College of Veterinary Medicine. Jour. of Vet. Med. p. 569–872 (Sep. 15, 1981). Fraiz, J. R., Jones, B., Chlamydial Infections. Ann. Rev. Med. 39:357–70 (1988). Fudge, A. M. Update on Chlamydiosis. Vet. Clin. of N. Amer. Small Animal Practice. 14(2):201–21 (March 1984). Johnson, F. W. A., Matheson, B. A., Williams, H., Laing, A. G., Jandial, V., Davidson-Lamb, R., Halliday, G. J., Hobson, D., Wong, S. Y., Hadley, K. M., Moffat, M. A. J., Poslethwaite, R. Abortion Due to Infection with *Chlamydia psittaci* in a Sheep Farmer's Wife. British Med. Jour. 290:592–94 (Feb. 23, 1985). Moran, R. Epidemiologic and Laboratory Observation of *Chlamydia psittaci* Infections in Pet Birds. Jour. of Amer. Vet. Med. Assn. 184(11):1372–4 (Jun. 1, 1984). Nagington, J. Psittacosis/Ornithosis in Cambridgeshire. 1975–1983. Jour. Hyg. Camb. 92:9–19. Yung, A. P., Grayson, M. L., Psittacosis—a Review of 135 Cases. The Med. Jour. of Australia 148:228–33 (Mar. 7, 1988). Favero, M. S., Biological Hazards in the Laboratory. Lab. Med., 18(10):665–70 (Oct. 1987). Filstein, M. R., Ley, A. B., Vernon, M. S., Goffney, A., Glickman, L. T. Epidemic of Psittacosis in a College of Veterinary Medicine. J. Vet. Med. p. 569–72 (Sep. 15, 1981). Fraiz, J. R., Jones, B. Chlamydial Infections. Ann. Rev. Med. 39:357–70 (1988).

Chlamydial infections are recognized in at least 130 species of birds and the transmission from birds to man is well documented. Various strains of *Chlamydia psittaci* are well recognized as causing disease syndromes in a wide variety of mammalian species and *Chlamydia psittaci* infections in humans have been epidemiologically linked to many of these sources. Fudge, A. M., Update on Chlamydiosis. Vet. Clin. of N. Amer. Small Animal Practice, 14(2):201–21 (March 1984). Moran, R., Epidemiologic and Laboratory Observation of *Chlamydia psittaci* Infections in Pet Birds. Jour. of Amer. Vet. Med. Assn. 184(11):1372–4 (Jun. 1, 1984). Nagington, J. Psittacosis/Ornithosis in Cambridgeshire. 1975–1983. Jour. Hyg. Camb. 92:9–19.

Vaccines against chlamydia have been disclosed. In particular, two proteins of molecular mass of 18,000 daltons and 31,000 daltons are known to be associated with infectious elementary bodies of *C. trachomatis* have been found to bind to eukaryotic cells. These proteins are thought to be of particular interest because the attachment of the pathogen to its host cell is critical to successful invasion of the elementary bodies. Antibodies raised against these proteins possess neutralizing activity, which may indicate a protective role for such antibodies. Purified 18 kilodalton *C. trachomatis* extra cellular binding protein substantially free of other *C. trachomatis* proteins in a pharmaceutically acceptable carrier and purified 31 kilodalton *C. trachomatis* extracellular binding protein substantially free of other *C. trachomatis* proteins in a pharmaceutically acceptable carrier have been disclosed as vaccines. EPA 0,293,079.

Previous molecular work with the subunits of Chlamydia biovars other than *C. psittaci* has, for the most part, been limited to a major outer membrane protein that has a molecular weight from 42 to 45 kilodaltons occupying 60 percent of the outer membrane and a 15 kilodaltons lipopolysaccharide that is known to be genus specific. Batteiger, B. E., Newhall V, W. J., Terho, P., Wilde III, C. E., Jones, R. B.: Antigenic Analysis of the Major Outer Membrane Protein of *Chlamydia trachomatis* with Murine Monoclonal Antibodies. Infect. Immun. 53(3)530–3 (1986). Bavoil, P., Ohlin, A., Schachter, J.: Role of Disulfide Bonding in Outer Membrane Structure and Permeability in *Chlamydia trachomatis*. Infect. Immun. 44(2):479–85 (1984). Brade, L., Schramek, S., Schade, U., Brade, H.: Chemical, Biological, and Immunochemical Properties of the *Chlamydia psittaci* Lipopolysaccharide. Infect. Immun. 54(2):568–74 (Nov. 1986). Caldwell, H. D., Judd, R. C.: Structural Analysis of Chlamydial Major Outer Membrane Proteins. Infect. Immun. 38:960–8 (Dec. 1982). Caldwell, H. D., Schachter, J.: Antigenic Analysis of the Major Outer Membrane Protein of Chlamydia spp. Infect. Immun. 35(3):1024–31 (Mar. 1982). Caldwell, H. D., Kromhout, J., Schachter, J.: Purification and Partial Characterization of the Major Outer Membrane Protein of *Chlamydia trachomatis*. Infect. Immun. 31(3):1161–76 (1981). Carlson, E. J., Peterson, E. M., de la Maza, L. M.: Cloning and Characterization of a *Chlamydia trachomatis* L3 DNA Fragment That Codes for an Antigenic Region of the Major Outer Membrane Protein and Specifically Hybridizes to the C- and C-Related-Complex Serovars. Infect. Immun. 57(2):487–94 (1989). Conlan, J. W., Clarke, I. N., Ward, M. E.: Epitope Mapping with Solid-Phase Peptides: Identification of Type-, Subspecies-, Species- and Genus-Reactive Antibody Binding Domains on the Major Outer Membrane Protein of *Chlamydia trachomatis*. Molecular Microbiology. 2(5):673–9 (1985). Ma, J. J., Chen, K. C. S., Kuo, C.: Identification of Conserved Regions for Species and Subspecies Specific Epitopes on the Major Outer Membrane Protein of *Chlamydia trachomatis*. Micro. Pathogenesis 3:299–307 (1987). Nano, F. E., Barstad, P. A., Mayer, L. W., Coligan, J. E., Caldwell, H. D.: Partial Amino Acid Sequence and Molecular Cloning of the Encoding Gene for the Major Outer Membrane Protein of *Chlamydia trachomatis.* Infect. Immun. 48(2):372–7 (1985). Pickett, M. A., Ward, M. E., Clarke, I. N.: High-level Expression and Epitope Localization of the Major Outer Membrane Protein of *Chlamydia trachomatis* Serovar L1. Molecular Microbiology. 2(5):681–5 (1988). Stephens, R. S., Wagar, E. A., Schoolnik, G. K.: High-Resolution Mapping of Serovar-Specific and Common Antigenic Determinants of the major Outer Membrane Protein of *Chlamydia Trachomatis.* J. Exp. Med. 167:817–31 (1988). Su, H., Zhang, Y., Barrera, O., Watkins, N. G., Caldwell, H. D.: Differential Effect of Trypsin on Infectivity of *Chlamydia trachomatis:* Loss of Infectivity Requires Clevage of Major Outer Membrane Protein Variable Domains II and IV. Infect. Immun. 56(8):2094–100 (1988). Tan, T., Herring, A. J., Anderson, I. E., Jones, G. E.: Protection of Sheep Against *Chlamydia psittaci* Infection with a Subcellular Vaccine Containing the Major Outer Membrane Protein. Infect. Immun. 58(8):3101–8 (1990). Taylor, H. R., Prendergast, R. A.: Attempted Oral Immunization with Chlamydial Lipopolysaccharide Subunit Vaccine. Invest. Ophthalmol. Vis. Sci. 28(10):1722–6 (Oct. 1987). Taylor, H. R., Prendergast, R. A.: Oral Immunization with Chlamydial Major Outer Membrane Protein (MOMP). Invest. Ophthalmol. Vis. Sci. 29(12):1847–53 (Dec. 1988). Zhang, Y., Stewart, S., Joseph, T., Taylor, H. R., Caldwell, H. D.: Protective Monoclonal Antibodies Recognize Epitopes Located on the Major Outer Membrane Protein of *Chlamydia trachomatis*[1]. J. Immun. 138:575–81 (1987). The above discussed work with the major outer membrane proteins, however, have not yet proven to be efficacious when utilized as a vaccine.

The polypeptide vaccine described in this application has shown, by an initial multiple challenge, to be highly protective against Chlamydia infection. Surprisingly, it was found that a 96 kilodalton polypeptide and certain associated polypeptides that includes the extracellular binding protein and other related proteins of ATCC strain DD-34 are highly antigenic and can provide protection from a variety of Chlamydia strains.

SUMMARY OF THE INVENTION

It is an object of this invention to make a polypeptide vaccine that protects several animal species against infection by Chlamydia. To achieve the objects of this invention and in accordance with the purposes of the present invention a 96 kilodalton polypeptide, of the *Chlamydia psittaci* strain DD-34 was isolated along with other polypeptides ranging in size from 40–140 kilodalton.

In particular, this invention is directed to a vaccine for treating patients to protect against a Chlamydia infection comprising administering an effective amount of a polypeptide as described herein above in a physiologically acceptable diluent. This invention further relates to a subunit vaccine against *Chlamydia psittaci* strain DD-34, wherein the polypeptides are reactive with antibodies secreted by hybridoma ATCC no. HB10861.

DETAILED DESCRIPTION OF THE INVENTION

Reference will now be made in detail to the presently preferred embodiments of the invention, which, together with the drawings and the following examples, serve to explain the principles of the invention.

As noted above, the present invention relates principally to a 96 kilodalton polypeptide, and to other polypeptides ranging from about 40 to 140 kilodaltons that are useful, for immunization against Chlamydia. In the examples, polypeptides ranging from 40 to 140 kilodaltons of strain DD-34 were used. It should be understood that in other embodiments the subunit vaccine may comprise the combination of the 42 and 96 kilodalton polypeptides and, in another embodiment the subunit vaccine may include only the 96 kilodalton polypeptide. It should be noted, however, that the molecular weights disclosed herein are not to be interpreted as absolute values.

The high degree of antigenicity and cross reactivity of these polypeptides gives evidence of their ability to stimulate a strong immune response when purified and mixed with a suitable adjuvant. Since this is a subunit vaccine it could be useful in several species of animals, and against several different biovars of chlamydia, without the delayed type hypersensitivity reaction or anamnestic responses reported with whole organism vaccines.

The polypeptides of the present invention are capable of forming "neutralizing antibodies" i.e. antibodies that will protect against *Chlamydia psittaci* and *Chlamydia trachomatis* in a variety of animals. In particular, the polypeptides have been found to be useful for immunizing against a bovine respiratory, DD-34, mouse pneumonitis, and guinea pig conjunctivitis strains of Chlamydia. Accordingly, the present invention is also directed to methods of protecting a patient against contracting *Chlamydia psittaci* and *Chlamydia trachomatis*.

The active component of the vaccine according to the invention can be employed with a physiologically acceptable diluent (medium), e.g. phosphate buffered saline. The vaccine may possibly be administered by subcutaneous, intradermal, intranasally or intramuscular injection, or as a water additive. Frequency of administration will vary depending upon the vaccine.

As a subunit vaccine, it is envisioned that the above described invention would afford protection to several species of animals such as mouse, guinea pig, cow and man. It is also expected to protect against several different biovars of Chlamydia, without the delayed type hypersensitivity reaction or anamnestic response reported with whole organism vaccines.

It should be understood that these specific antigenic epitopes can be made by recombinant DNA techniques or synthetic peptides. Baehr et al: Proc. Nat'l. Acad. Sci. USA 85:4000–4 (1988); Stephens et al.: J. Exp. Med. 167:817–31 (1988).

EXAMPLE 1

Hybridoma Production

Whole elementary bodies (ATCC No. VR854—Strain DD-34) were inactivated with a 1% solution of binary ethyleneamine at 37° C. for 24 hours (Larghi and Nebel, 1988; Larghi et al., 1976). Residual binary ethyleneamine was inactivated by a 1% solution of sodium thiosulfate (Larghi and Nebel, 1988; Larghi et al., 1976). One ml of inactivated elementary bodies containing 8.9 mg protein was mixed with 1 ml of physiological saline, added to a vial of RIBI adjuvant (ImmunoChem, Hamilton, Mont.) and warmed to 37° C. in a water bath prior to mouse inoculation.

Three-month old female Balb/C mice were injected intraperitoneally with 0.2 ml of the elementary body-adjuvant solution. One injection was given weekly for a total of three injections. A fourth injection without RIBI adjuvant was given intraperitoneally four days before fusion. The hyperimmunized spleen cells were fused with AG8 myeloma cells with the aid of polyethylene glycol. After four fusions and the production of approximately 1,600 hybridomas, 19 were identified as rapid growers. These 19 hybridomas were cloned when appropriate by limiting dilution.

EXAMPLE 2

Isotyping and Subisotyping Supernatants

Supernatants from the 19 hybridomas obtained in Example 1 were isotyped using an isotyping reagent kit (Hy Clone Laboratories, Logan, Utah) and subisotyped using a reagent kit (Calbiochem Corp., LaJolla, Calif.), according to the manufacturers' recommended protocols. Briefly, the supernatants were isotyped by coating 96-well microtiter plates with 100 µl of a plate coating solution containing 1% goat anti-mouse immunoglobulins. Excess solution was removed by tapping on absorbent paper before filling the wells with a phosphate-buffered saline-surfactant solution to reduce non-specific binding. Next, 50 µl of phosphate-buffered saline-surfactant and 50 µl of hybridoma supernatant was placed in the wells along with positive and negative controls. A peroxidase conjugate and a substrate composed of a concentrate of citrate buffer containing a 1% urea peroxide was used with O-phenylene diamine as a chromophobe.

For subisotyping, a plate coating solution containing 1% goat anti-mouse immunoglobulins was used to coat a 96-well microtiter plate. The supernatants were diluted with phosphate-buffered saline-surfactant solution and added to the plate. After washing, typing antisera was placed in the wells for testing the supernatants, and phosphate-buffered saline-surfactant was used for negative controls. A peroxidase conjugate was used followed by a 1% urea peroxide substrate and O-phenylene diamine as a chromophobe. The results of isotyping and subisotyping are reported in Table I, below.

TABLE I

Immunoglobulin types and assay reactions of the 19 monoclonal antibodies

| Clone supernatants | Isotype/ subisotype | ELISA | Dot blot assays | |
| --- | --- | --- | --- | --- |
| | | | Native elementary bodies proteins | Solubilized elementary bodies proteins |
| 2-1 F10 | IgM | − | − | − |
| 2-15 E3 | IgG1 | + | + | + |
| 2-11 F10 | IgG1 | + | − | − |
| 3-8 C8 | IgM | weak + | − | − |
| 2-11 E9 | IgG2a | weak + | − | − |
| 4-5 F3 | IgG1, IgM | + | − | − |
| 4-6 B6 | IgM | + | − | − |
| 4-7 D10 | IgM | + | − | − |
| 4-8 G11 | IgG3, IgM | weak + | − | − |
| 4-10 B8 | IgM | weak + | − | − |
| 4-11 D8 | IgG3 | + | − | − |
| 4-12 B4 | IgM | + | + | − |
| 4-12 B5 | IgG3, IgM | weak + | − | − |
| 4-14 B9 | IgG3, IgM | + | + | − |
| 4-14 D11 | IgG1 | weak + | − | − |
| 4-16 G3 | IgM | weak + | − | − |
| 4-17 B2 | IgG2b, IgM | + | − | − |
| 4-17 B8 | IgG1, IgM | − | − | − |
| 4-7 D10 | IgM | weak + | − | − |

EXAMPLE 3

Enzyme Linked Immunosorbent Assay to Native Proteins

The hybridoma supernatants of Example 2 were further characterized by use of a mouse IgG, enzyme immunoassay, hybridoma screening kit according to the manufacturer's recommendations (Vector Laboratories, Burlingame, Calif.). Briefly, whole elementary bodies of C. psittaci strain DD-34 were diluted 1 to 250 in deionized distilled water and 100 µl was placed in each well of a 96-well microtiter plate (Midland Scientific, Inc., Omaha, Nebr.). Elementary bodies (ATCC No. VR854 Strain DD-34) were diluted 1 to 10 in a solution containing 0.218 molar sucrose, 0.0038M $KH_2PO_4$, 0.0072M $K_2HPO_4$, and 0.0049M phosphate glutamate sucrose. The phosphate glutamate sucrose solution had been autoclaved at 10 pound pressure for 10 minutes and the pH adjusted to 7.0 with 2N KOH prior to use. Yolk sacs of 7-day-old specific pathogen-free chicken eggs (Spafus, Inc., Roanoke, Ill.) were injected with 0.4 ml of the dilution of 1 to 10 elementary bodies-phosphate glutamate sucrose solution. Embryos that died within three days were discarded and assumed dead of bacterial contamination or trauma. Yolk sac membranes of all eggs that lived past three days were harvested on day seven, mixed with phosphate glutamate sucrose to make a 20% yolk sac membrane solution, homogenized and centrifuged at 300×G for 10 minutes at 4° C. The centrifugate contained three layers. The middle layer containing the elementary bodies was removed with a pipette and purified through RENOGRAFIN 60 (Squibb, New Brunswick, N.J.) density gradients, consisting of 22 ml of 20% RENOGRAFIN on top of 5 ml of 50% RENOGRAFIN. These gradients were centrifuged at 63,500×G for one hour at 4° C. The elementary body fraction collected at the 50% RENOGRAFIN (Squibb) interface. The elementary bodies were removed by drip fractionation and pelleted through calcium-magnesium-free phosphate-buffered saline by centrifuging at 49,200×G for 20 minutes at 4° C. Each pellet was resuspended in 1 ml of calcium-magnesium-free phosphate-buffered saline and frozen at −70° C.

The plate was sealed with cellophane tape and placed on a shaker in a 37° C. incubator overnight. Supernatants from each of the 19 hybridomas were diluted 1 to 250 and 100 μl of each was assayed in replicates of five. The assay was done using a biotinylated anti-mouse IgG in phosphate-buffered saline containing 1% normal bovine serum, followed by an avidin-enzyme system with a 2,2'azino-di (3-ethyl benthiazolin-sulfate) substrate. The results were read on a BIO-TEK EL-380 ELISA Reader at 405 nm (BIO-TEK, Winooski, Vt.) and are reported in Table I, above.

EXAMPLE 4

Dot Blot Assay with Native Chlamydial Proteins

A BIO-DOT (Bio-Rad) apparatus was used with a 0.2μ pore size nitrocellulose membrane. The membrane was presoaked in Tris buffered saline consisting of 0.016M Tris HCl and 0.5M NaCl, pH 7.5 prior to its placement in the BIO-DOT (Bio-Rad) apparatus. One hundred μl of a 1 to 250 dilution of whole elementary bodies of DD-34 Chlamydial proteins inactivated with binary ethyleneamine was placed in each well and allowed to gravity flow through the membrane. Next, 200 μl of 1% bovine serum albumin in Tris buffered saline was allowed to gravity flow through the membrane to block any unbound sites. This was followed by two washes with 200 μl of a solution consisting of Tris buffered saline containing 0.05% Tween 20. The supernatants from the 19 hybridomas were diluted 1 to 250 in an antibody solution consisting of 1% bovine serum albumin in Tris buffered saline containing 0.05% Tween 20. One hundred μl of each diluted supernatant was applied to the membrane in replicates of five and allowed to gravity flow.

This was followed by three washes with Tris buffered saline containing 0.05% Tween 20. The membrane was removed from the apparatus and washed two more times in a glass dish with Tris buffered saline containing 0.05% Tween 20. Next, the membrane was treated with 5 µg of biotinylated secondary antibody in Tris buffered saline containing 0.05% Tween 20 and agitated on a shaker platform for 30 minutes. This was followed by two washes with Tris buffered saline containing 0.05% Tween 20 and two washes with Tris buffered saline before being incubated in an avidin biotin complex for 30 minutes with gentle shaking. The membrane was washed two times with Tris buffered saline containing 0.05% Tween 20 and two times with Tris buffered saline. A diaminobenzidine plus nickel chloride substrate was added. After development, the reaction was stopped by washing with deionized distilled water.

To insure enough protein to be recognized by the antibodies was sticking to the membrane, dilutions of 1 to 10 to 1 to 1,500 were run through a membrane and stained with Jansons Aurodye Forte protein stain (Bio-Tek, Winooski, Vt.). The results are reported in Table I, above.

EXAMPLE 5

Dot Blot Assay to Solubilized Proteins

The same protocol for the dot blot to native proteins was followed except the chlamydia elementary bodies were boiled for 10 minutes prior to running the assay. The results are reported in Table I, above. It is apparent from Table I that the only clone to recognize the Chlamydia elementary body proteins in all assays was 2–15 E3. This alone has been assigned ATCC No. HB10861. Out of four fusions and the production of approximately 1,600 hybridomas, 17 hybridoma supernatants reacted with varying degrees in the ELISA of Example 3 to whole chlamydial elementary bodies. After further screening, three supernatants bound to whole elementary bodies by both ELISA and dot blot to nitrocellulose, however, when the elementary bodies were solubilized by boiling for 10 minutes and dot blotted, only the supernatant from hybridoma 2–15 E3 reacted. Apparently, the epitope recognized by this monoclonal antibody was persistent after solubilization while the epitopes recognized by the other three monoclonal antibodies were destroyed or altered in such a way that they were no longer recognized.

Hybridoma 2–15 E3 produces monoclonal antibodies that identify strains of both *Chlamydia psittaci* and *Chlamydia trachomatis* isolates when tested by an enzyme linked immunosorbent assay and a nitrocellulose membrane dot blot assay. By sodium dodecyl sulfate polyacrylamide gel electrophoresis, the target polypeptide of 2–15 E3 was found to be in approximately the 96 kilodalton molecular weight range. The hybridoma that secretes this monoclonal antibody was deposited on Aug. 28, 1991, under the conditions of the Budapest Treaty with the American Type Culture Collection, Rockville, Md., and has been assigned ATCC Accession No. HB10861.

EXAMPLE 6

Reactivity Testing

The monoclonal antibody secreted by clone ATCC No. HB10861 was found to be able to detect a variety of *Chlamydia psittaci* strains: B577, 1PA, Borg, E58 (McNutt), CP-3, Texas Turkey, No. 1, *Chlamydia trachomatis* strains: TWAR 434, LGV—Type II all obtained from the American type culture collection and KSU89-3720, KSU88-15974 and KSU89-13400 isolated by Kansas State University. Other bacteria tested, however, had no cross reactivity: *E. coli* hemolytic, K88T, *E. coli* nonhemolytic, mucoid, *E. coli* nonhemolytic, nonmucoid, *Pasteurella hemolytica*, *Pasteurella multocida*, *Moraxella sp.*, *Klebsiella pneumoniae*, *Klebsiella bronchiseptica*, *Alcalgienes faecalis*, *Staphylococcus aureus*, *Streptococcus suis*, *Citrobacter sp.*, *Acinetobacter lwoffi*, *Proteus mirabilis*, *Enterobacter cloacae*, *Enterobacter agglomerans*, *Pseudomonas aeruginosa*, *Salmonella sp.*, *actinobacillus equuli*, Actinobacillus, and Haemophilus.

It appears from these studies that the 96 kilodalton peptide contains an epitope common to various strains of Chlamydia in different animals.

EXAMPLE 7

Sodium Dodecyl Sulfate Polyacrylamide Gel Electrophoresis and Immunoblotting of Strains, DD-34, Borg and Host Proteins Electrophoresis was conducted as described by Laemmli (1970). Protein contents of 20 µg of *C. psittaci* strain DD-34, *C. psittaci* strain Borg, yolk sac membrane, chick embryo tissue and albumin were separated by sodium dodecyl sulfate polyacrylamide gel electrophoresis, transferred to 0.2µ nitrocellulose (American Bionetics, Inc., Hayward, Calif.) and Western blotted with monoclonal antibody 2–15 E3 and polyclonal antibodies to evaluate possible cross reactivity of the antibodies.

Electrophoresis sample buffer consisted of 0.121M Tris base, 0.001M ethylenediaminetetraacetate, 1% sodium dodecyl sulfate. Prior to loading, the gels were pre-run for 30 minutes at 10 ma constant current for each gel and electrophoresis was carried out at 30 ma constant current for each gel until proteins were near the bottom edge. The molecular weight marker lanes were removed and stained with a colloidal gold reagent (Jansens Auro Dye Forte protein stain, Olen, Belgium). The test proteins were probed with an immunoperoxidase system and a diaminobenzidine-nickle chloride substrate (Vector Laboratories, Burlingame, Calif.).

EXAMPLE 8

Western Blot of *C. psittaci* Strains DD-34 and Borg

The Western blotting showed that 2–15 E3, which reacted to solubilized proteins of *C. psittaci* DD-34 by dot blot, also probed for a 96 kilodalton protein of strain Borg; however, no probing was evident to the strain DD-34. Further blotting with a murine polyclonal antibody made to DD-34 whole elementary bodies also probed for the 96 kilodalton protein and faintly for a protein in the 60 kilodalton range of Borg with no probing for any of the DD-34 proteins.

Both Chlamydial strains studied apparently share an antigenic epitope that is recognized by 2–15 E3 using an ELISA, and in the native or solubilized form when dot blotted to nitrocellulose; however, this epitope is persistent only in Borg after electrophoresis and transfer. By linearization of the proteins in preparation for sodium dodecyl sulfate polyacrylamide gel electrophoresis, the antigenic polypeptide is apparently altered beyond recognition in strain DD-34 but persists in strain Borg; however, there appears to be enough reassociation of the solubilized proteins when dot blotted for the epitope to be recognized in strain DD-34 as well as Borg.

The 96 kilodalton protein of strain DD-34 appears from this study, to be a strong antigen. The epitope recognized by 2–15 E3 has been shown to exist in both the binary ethyleneamine inactivated form and the noninactivated form.

EXAMPLE 9

Vaccine Trials

The polypeptides used in the vaccine trials were isolated by sodium dodecyl sulfate polyacrylamide gel electrophoresis. Polypeptides ranging from a 40 to 140 kilodaltons of strain DD-34 were excised from the sodium dodecyl sulfate polyacrylamide gel electrophoresis, electroeluted and vacuum desiccated at room temperature to a reading of 446 on the dryness scale. These polypeptides were selected to provide support and adhesion for the antigenic 96 kilodalton polypeptide. The high degree of antigenicity and cross-reactivity of this polypeptide gives evidence of its ability to stimulate a strong immune response when purified and mixed with a suitable adjuvant. These polypeptides were rehydrated with RIBI adjuvant, MPL+TDM+CWS to make the test vaccine.

Three injections were given to four guinea pigs weighing approximately 700 g. These consisted of two injections of 0.2 cc given subcutaneously, in two different sites and one injection of 0.1 cc given intraperitoneally for a total of 1 mg protein. Two weeks after the booster injection, the four vaccinated guinea pigs and one nonvaccinated guinea pig was challenged with guinea pigs inclusion conjunctivitis-vaginitis chlamydial elementary bodies (grown, isolated, and purified as previously described). This first challenge consisted of 0.1 ml intraocularly and 0.1 ml intravaginally. Another intranasal challenge was conducted three weeks after the first. This challenge consisted of 0.15 ml of a respiratory strain of Chlamydia elementary bodies that were isolated from a bovine with pneumonia. One week later, the guinea pigs were anesthetized with ether and 0.2 cc were injected into the right lung of each guinea pig using a 25 gauge, 1" needle. Three weeks later the guinea pigs were subjected to a second challenge using a highly zoonotic parrot strain (DD-34) of Chlamydia. The guinea pigs were again anesthetized with ether and 1 cc was injected into the right lung by hypodermic needle. This was expected to be a terminal challenge because of the pathogenicity of this agent. All challenge materials consisted of approximately 10 mg of protein per ml. There were no clinical signs in any of the vaccinated guinea pigs—they continued the same pattern of food and water consumption.

The nonvaccinated guinea pig began to loose weight shortly after the first challenge, show severe respiratory signs, and symptoms of central nervous system disorders. All guinea pigs were euthanatized and necropsied. Tissues were taken and tested for chlamydial proteins using an enzyme-linked immunosorbent assay and an immunogold silver enhanced technique for tissues and secretions. Additionally, histopathological studies of tissue were documented. On gross pathology examination, the vaccinated guinea pigs showed no visible lesions. The right lung of the nonvaccinated guinea pig was blackened and apparently nonfunctional. Also, the plural cavity contained a large quantity of serofibrinous fluid. The pericardial sac also contained fibrinous fluid. The uterus of the nonvaccinated guinea pig was enlarged, and darkened. Liver and lung tissues of all guinea pigs were examined by ELISA for chlamydial proteins using the 2–15 E3 monoclonal antibody described in Examples 2–5. The lungs of all guinea pigs were found to contain chlamydial proteins; however, only the nonvaccinated guinea pig contained chlamydial proteins in the liver. This was evidence that the Chlamydia challenge had become a systemic infection only in the nonvaccinated animal. The monoclonal antibody utilized in the ELISA will detect the 96 kilodalton polypeptide, even if the chlamydial elementary body has been destroyed by circulating antibodies or macrophages.

It will be appreciated that the instant specification and claims are set forth by way of illustration and not limitation, and that various modifications and changes may be made without departing from the spirit and scope of the present invention.

I claim:

1. A subunit vaccine against Chlamydia infection comprising (1) a pharmaceutically acceptable carrier and (2) a polypeptide fraction of *Chlamydia psittaci* strain DD-34 consisting of polypeptides having molecular weights of between about 40 and 140 kilodaltons, said fraction comprising a polypeptide having a molecular weight of about 96 kilodaltons.

2. The vaccine of claim 1 wherein said polypeptide fraction consists of polypeptides having molecular weights of about 42 kilodaltons and about 96 kilodaltons.

3. A subunit vaccine against Chlamydia infection comprising (1) a pharmaceutically acceptable carrier and (2) a polypeptide having a molecular weight of about 96 kilodaltons from *Chlamydia psittaci* strain DD-34.

4. A subunit vaccine against Chlamydia infection consisting essentially of an isolated or purified polypeptide of *Chlamydia psittaci* strain DD-34 that is reactive with the antibody secreted by hybridoma ATCC No. HB10861.

5. The vaccine of any one of claims 1, 2, 3 or 4, further comprising an adjuvant.

6. A method of immunizing a subject against Chlamydia comprising administering an effective amount of the vaccine of claim 5.

7. A method of immunizing a subject against Chlamydia comprising administering an effective amount of the vaccine of claim 1.

8. A method of immunizing a subject against Chlamydia comprising administering an effective amount of the vaccine of claim 2.

9. A method of immunizing a subject against Chlamydia comprising administering an effective amount of the vaccine of claim 3.

10. A method of immunizing a subject against Chlamydia comprising administering an effective amount of the vaccine of claim 4.

* * * * *